United States Patent [19]

Rose et al.

[11] Patent Number: 5,703,101

[45] Date of Patent: *Dec. 30, 1997

[54] AGONIST-ANTAGONIST COMBINATION TO REDUCE THE USE OF NICOTINE AND OTHER DRUGS

[75] Inventors: Jed E. Rose, Venice; Edward D. Levin, Los Angeles, both of Calif.

[73] Assignee: Robert J. Schaap; a part interest

[*] Notice: The term of this patent shall not extend beyond the expiration date of Pat. No. 5,316,759.

[21] Appl. No.: 570,530

[22] Filed: Dec. 11, 1995

Related U.S. Application Data

[63] Continuation of Ser. No. 235,454, Apr. 29, 1994, Pat. No. 5,574,052, which is a continuation of Ser. No. 54,144, Apr. 30, 1993, which is a continuation of Ser. No. 855,868, Mar. 23, 1992, Pat. No. 5,316,759, which is a continuation of Ser. No. 231,092, Aug. 11, 1988, abandoned, which is a continuation-in-part of Ser. No. 840,072, Mar. 17, 1986, Pat. No. 4,846,199.

[51] Int. Cl.$^6$ .......................... A61K 31/44; A61K 31/465
[52] U.S. Cl. .......................... 514/343; 131/270; 131/271; 131/329; 424/10; 514/660; 514/810; 514/812; 514/813; 514/922; 514/947
[58] Field of Search ....................... 514/343, 660, 514/810, 812, 813, 922, 947; 424/10; 131/270, 271, 329

[56] References Cited

U.S. PATENT DOCUMENTS

| 5,316,759 | 5/1994 | Rose et al. ................ 514/343 |
| 5,480,651 | 1/1996 | Callaway .................. 424/464 |

*Primary Examiner*—Herbert J. Lilling

[57] ABSTRACT

A method of treating and reducing a drug dependency such as a nicotine dependency is provided. The method comprises initially administering to a subject a drug, such as nicotine or another agonist of the drug in an amount which would normally provide the desired pharmacologic effects and at least partially satiate the needs for the drug by a user. The method also comprises administering to the subject an antagonist to the drug or its other agonist in an amount sufficient to at least partially block the pharmacologic effects of the drug or its other agonist. In one embodiment of the invention, the drug and the antagonist are administered substantially simultaneously so as to occupy a substantial portion of the receptors of the user for that drug thereby blocking or attenuating the effects of any further intake of the drug or other agonist. In another embodiment, the drug or its other agonist is first administered and the antagonist is self-administered by a subject in a manner which mimics the use of the drug thereby counter-conditioning the drug user to the stimuli associated with the normal administration of the drug. The invention further provides a method of therapeutically treating psychophysiologic diseases and disorders involving neuronal dysregulation. The method additionally provides a pharmacologic composition for the treatment and reduction of drug dependence and which relied upon a combination of an agonist and an antagonist.

18 Claims, 2 Drawing Sheets

AGONIST-ANTAGONIST COMBINATION TO REDUCE THE USE OF NICOTINE AND OTHER DRUGS

RELATED APPLICATIONS

This application is a continuation of our U.S. patent application Ser. No. 235,454, filed Apr. 29, 1994 for "Agonist-Antagonist Combination To Reduce The Use Of Nicotine And Other Drugs" now U.S. Pat. No. 5,574,052 which is a continuation of our U.S. patent application Ser. No. 054,144, filed Apr. 30, 1993, for "Agonist-Antagonist Combination To Reduce The Use Of Nicotine And Other Drugs", which was a continuation of our U.S. patent application Ser. No. 855,868, filed Mar. 23, 1992 for "Agonist-Antagonist Combination To Reduce The Use Of Nicotine And Other Drugs", now U.S. Pat. No. 5,316,759 which was a continuation of our U.S. patent application Ser. No. 231,092, filed Aug. 11, 1988; for "Agonist-Antagonist Combination To Reduce The Use Of Nicotine And Other Drugs", (now abandoned) which is a continuation-in-part of patent application Ser. No. 840,072, filed Mar. 17, 1986, entitled "Smoking of Regenerated Tobacco Smoke" (now U.S. Pat. No. 4,846,199, dated Jul. 11, 1989).

GOVERNMENT RIGHTS

This invention was made with the support of the Veterans Administration of the United States government. The government has certain rights in this invention.

BACKGROUND OF THE INVENTION

1. Field of the Invention

This invention relates in general to certain new and useful improvements in methods and compositions for treating and reducing drug dependency and for therapeutically treating psychophysiologic diseases and disorders involving neuronal dysregulation and more particularly, to methods and compositions of the type stated which rely upon the administration of a combination of a drug or another agonist and an antagonist to the drug.

2. Brief Description of the Prior Art

The substantial use of drugs and particularly, the widespread abuse of drugs has led to increased incidence of health problems and has even largely contributed to significant increases in crime. It has been well established that the intake of the drug nicotine through tobacco smoking has resulted in various adverse health conditions. While the use of drugs, such as nicotine, do not necessarily lead to increased incidence of crime, use of this drug and similar related drugs does present significant health problems.

While the use of other addictive drugs including controlled substances such as various narcotics, e.g., heroin and cocaine, also can result in adverse health conditions, these more serious drug uses have a significant social impact in that they give rise to a substantial increase in numerous types of criminal activity. Various governmental agencies have expended substantial sums of money in attempting to eradicate or at least reduce the incidence of crime, but without much success. Accordingly, in recent years, there has been an increased emphasis on attempting to treat and reduce drug dependency.

The use of drugs is also involved in the treatment of various psychophysiologic disorders, and particularly psychiatric disorders involving dysregulation of a neurotransmitter. In addition, certain diseases involving imbalances of the autonomic nervous system are treated by administration of certain drugs. Here again, these drugs may have serious side effects in that while they may attenuate a certain disorder, they exacerbate other disorders. Further, many of the drugs used to treat these disorders can produce dependence as for example a dependence on diazepam (Valium). Therefore, the subject, while finding some release from the disorder or disease, may become severely addicted to the drug which is used.

In general, two approaches have been used in the pharmacologic treatment of drug dependence. The first approach is often described as the "substitution approach" and provides an alternative drug which is designed to theoretically allow the user to withdraw from the habitually abused drug without suffering the aversive symptoms normally associated with a withdrawal from a drug. As a simple example, methadone is often administered to heroin addicts in the treatment of heroin addiction. It was anticipated and initially believed that a substitution of methadone for heroin, for example, would lead to the eventual cessation of all drug use after a weaning period in which the dose of the substituted drug was gradually reduced.

This first approach to drug dependency has met a very low rate of success. It has been found that the substitution of one drug for another does not typically wean the subjects from all drugs. In fact, it has been found in many cases that the drug users will store the substituted drug, such as the methadone, and continue to use the more addictive drug, heroin or morphine, and only use the stored substitute, methadone, when the heroin or morphine is not readily available. Thus, this first approach to reduced drug dependency has met with very little success.

There have also been various proposed treatments for the administration of nicotine (the putative addictive substance in tobacco smoking) as a replacement for tobacco smoking. One of the most successful approaches which have been used to date in reducing the incidence of tobacco smoking relies upon nicotine containing chewing gum. The use of this type of gum suffers from several problems, including not only the bad taste and destruction of dental appliances, but the gastrointestinal upset which results therefrom and which also reduces compliance. Moreover, the nicotine containing chewing gums do not satisfy that craving which most smokers experience for the distinct sensations in the throat and chest elicited by the nicotine in smoke. Over the course of many years of tobacco smoking, these particular sensations have become an important part of and conditioned with the habit of smoking and help maintain tobacco smoke dependency.

There have also been several proposals for administering nicotine through various aerosol sprays. However, the aerosol sprays are designed to supply that amount of nicotine which would have been acquired by a user through the normal channel of tobacco smoking. The sprays result in severe respiratory tract irritation. There is no available means to provide the nicotine either by means of an oral or nasal spray and attenuate the severe irritating effects of the nicotine.

The second known general approach which has been used in the pharmacologic treatment of drug dependence involves the blocking of the reinforcing effects of the abused drug. It is theorized that by reducing the motivation of the user, there would be a reduced incidence of self-administration of a drug by the user. As a simple example, naltrexone is presently used to block the reinforcing effects of heroin and mecamylamine has been used to block the reinforcing effects of nicotine. This latter approach has not been found to be effective in that the intense withdrawal symptoms suffered by the user encourage compensating use of the addictive drug and thereby reduce compliance with the treatment unless a sufficient period of abstinence has elapsed so that the individual's nervous system is accustomed to the absence of the abused drug. The administration of an antagonist alone also creates a dysphoric state which encourages relapse and return to the abused drug.

Each of the aforementioned approaches have only been used experimentally. Moreover the individual antagonist approach and the individual agonist approach have each been found to be relatively ineffective. The second approach has been ineffective due to the fact that there are significant withdrawal or other adverse symptoms. This causes the drug abuser to return to his original drug habit in order to avoid the pain and discomfort associated with the withdrawal. Thus, this latter approach to reduce drug dependency has also met with little success.

Heretofore, no one has attempted to combine the sustained administration of a drug agonist and an antagonist to that drug in a therapeutic treatment. It would appear that the administration of an agonist and its antagonist would accomplish little, since the antagonist would effectively cancel out the effects of the agonist with a result that the combination would be equivalent to giving nothing at all.

OBJECTS OF THE INVENTION

It is, therefore, one of the primary objects of the present invention to provide a method of reducing the dependency on drugs by utilizing a combination of an agonist and an antagonist.

It is another object of the present invention to provide a method of the type stated for reducing drug dependency by simultaneously administering a drug or another agonist of that drug along with an antagonist to that drug and thereby occupy a substantial number of the receptors of a subject available to that drug or its agonist.

It is a further object of the present invention to provide a method of the type stated which enables administering an agonist and antagonist without causing an over-activity or under-activity of the receptor for the agonist thereby avoiding dangerous side effects which would occur if the agonist or antagonist were given alone in the same dosages.

It is a another salient object of the present invention to provide a method of the type stated in which a drug or another agonist of that drug is administered to an individual to provide a certain systemic level and an antagonist is self-administered by the individual which causes a reduction in the satisfaction associated with the intake of the drug or its other agonist.

It is also an object of the present invention to provide a method for treating psychophysiologic disorders and diseases involving neuronal dysregulation by the simultaneous application of an agonist and an antagonist in relative amounts so that substantial portions are present in the bloodstream in the patient having the disorder or disease.

It is an additional object of the present invention to provide a novel composition of a drug or another agonist of that drug and an antagonist to that drug.

With the above and other objects in view, our invention resides in the novel features of form and arrangement and combination of steps in the method and in the components forming part of the composition as hereinafter described.

BRIEF SUMMARY OF THE INVENTION

The present invention relates in general terms to a method of treating and reducing drug dependency. Any of a number of known drug dependencies can be treated in accordance with the method of the invention including for example, dependency on nicotine, heroin (or morphine) cocaine benzodiazepines and the like. The invention in a broad aspect relies upon a combination of an administration of a drug or another agonist of the drug and an antagonist to the drug. The present invention also provides a unique method of therapeutically treating psychophysiologic diseases and disorders involving neuronal dysregulation by a simultaneous administration of a drug or another agonist of the drug and an antagonist to the drug.

The term "agonist" is used in a broad sense and includes the drug of interest. Thus, for example, in this case, nicotine is an agonist and heroin is an agonist. Methadone is merely another agonist for heroin since it provides effects similar to that of heroin. Thus the term "agonist" as used herein, unless otherwise specified, will include the drug itself.

The method in a broad sense, comprises initially administering to a subject a drug or another agonist of this drug in an amount which would normally provide the desired pharmacologic effects. Moreover, the amount of the drug applied would at least partially satiate the needs for the drug by the user. The method also involves the administering to a subject an antagonist to the drug or its other agonist in an amount sufficient to at least partially block the pharmacologic effects of the drug or its other agonist while there is a substantial systemic amount of the drug or its agonist present.

The method of the present invention involves two general approaches to the treatment of drug dependency and to the therapeutic treatment of the above described psychophysiologic diseases and disorders which involve use of drugs. In the first approach, there is a treatment for the dependency on the drug by saturating a substantial portion of the known receptors for that drug with a combination of the drug or its other agonist and an antagonist to that drug or such other agonist. In this case, the agonist or drug is administered in an amount to which the subject is generally dependent upon that drug to thereby satisfy a demand for the drug. The antagonist is generally simultaneously administered to the same subject in an amount to attenuate the pharmacologic effects of the drug or its other agonist. In this case, the drug or its other agonist and the antagonist are preferably present in such an amount that more receptors of the drug are occupied by the drug and the antagonist than could safely be occupied by the drug alone or the antagonist alone. Moreover, a lesser number of the receptors are left available to respond to the drug thereby insulating the user from the reinforcing effects of the drug and at the same time minimizing adverse symptoms associated with the antagonist.

With the use of the current agonist-antagonist therapy one can attenuate the fluctuations of a neural system while keeping the absolute level of activation constant. In other words, one can attenuate the impact of an abused drug without causing a withdrawal syndrome and one can decrease the pathologically wide fluctuations in neural activity without adverse side effects associated with giving only an agonist.

In this case, the purpose of the invention is to saturate the receptors of the drug to thereby insulate the individual from the reinforcing effects of the drug. In the case of nicotine, the individual would be administered both nicotine and an antagonist to nicotine, such as mecamylamine. In the case of other drugs such as heroin, or its agonist, methadone, the antagonist naltrexone would be administered.

In accordance with this aspect of the invention, the drug may be present in an amount which would otherwise be toxic in the absence of the antagonist but the toxicity is offset by the presence of the antagonist. The drug should preferably be administered in a sufficiently high dose to occupy a sufficient number of the receptors and thereby substantially reduce a subject's demand for the drug.

In one preferred embodiment, both the drug, or its other agonist, and the antagonist may be administered by means of a transdermal patch, as hereinafter described in more detail. The drug or its other agonist and for that matter the antagonist, may be administered by other means such as oral administration, intravenous administration etc. In order to wean the person from the use of the drug, both the drug, or its other agonist, and the antagonist may be reduced in selected amounts over a period of time.

The use of this approach is effective in that the user will receive little or no satisfaction from taking additional amounts of the drug inasmuch as a very substantial portion of the receptors for that drug are already occupied by the initial dose of the drug and the initial dose of the antagonist to the drug.

The second general approach used in the administration of the agonist and an antagonist involves an inverse conditioning to the stimuli associated with the taking of the abused drug. In this case, the method involves the administering to a subject a drug or another agonist of the drug in an amount which would achieve a systemic level of the drug to which the subject was previously accustomed. This approach to the method also involves the self-administration of an antagonist to the drug or its other agonist, but only at selected intervals. Moreover, the antagonist is preferably administered in a form similar to the administration of the abused drug, as hereinafter described.

While this approach does increase the saturation of the receptors for the drug by the presence of the drug and the antagonist, it more importantly causes a reduction of the enjoyable effects associated with the taking of the drug. The subject is administered a certain amount of the drug or other agonist to provide a desired systemic level. The administration of the antagonist is preferably in a form with sensory cues which mimics or closely simulates the form in which the user was accustomed to taking the drug, as aforesaid. Thus, by taking the drug in this form, there is an inverse conditioning or counter-conditioning of the stimuli associated with the taking of the drug.

As a simple example of this latter approach in treating and reducing drug dependency, the dependency on nicotine could be reduced by providing a desired systemic level of the nicotine through a transdermal patch or other means. The antagonist, such as mecamylamine, could be incorporated into a smoking device, such as a simulated cigarette which provides many if not most of the sensory cues in normal tobacco smoking. In this way, when the user took a puff from the simulated cigarette, instead of receiving nicotine, he would receive an antagonist, namely the mecamylamine, thereby further depriving the user of the pharmacologic effects of nicotine to which he or she was previously accustomed. The usual conditioning is that smoking is associated with increased nicotine stimulation and pleasurable effects. However, in this case, smoking and its attendant sensory cues would be associated with decreased nicotine stimulation and the unpleasant effects of withdrawal whenever the user smoked.

It can be observed that one important factor in each of the above identified approaches to the method of the present invention is that there is generally a sustained level of the agonist in a user's bloodstream. When using the first approach, there would generally be a sustained level of both the agonist and the antagonist since they are generally simultaneously administered. In the second approach, there would at least be the sustained level of the agonist and the user would self-administer the antagonist at the will of the user. Thus, there would be peaks in the amount of the antagonist in the bloodstream of the user of the second approach.

Preferably, in both approaches to the method of the invention, the agonist is administered by a route which is different than that employed in the actual use of the drug. Thus, in the case of nicotine, administration of an agonist would occur by means of a transdermal patch or a route other than by way of smoking. In the case of the heroin, methadone would likely be used because it has a longer acting effect than heroin, but would be administered by a route different than the user employed for the administration of heroin. Thus, if the user self-administered heroin through a hypodermic needle, the methadone would be administered orally or by means other than a hypodermic needle. In this way, there will not be any reinforcement of the original response obtained by the common method of using the drug.

In both approaches, it can also be observed that there is essentially no self-administration of the agonist alone. In other words, the agonist may be self-administered in combination with the antagonist as for example, a composition in the form of a pill or tablet. Otherwise, the agonist would generally always be administered in a therapy, as for example, in a treatment center, or the like. The antagonist could be self-administered, as described above.

The present invention is also highly effective in the treatment of various psychophysologic disorders and diseases involving neuronal dysfunction, as described above. The invention utilizing both the agonist and the antagonist is effective in treating disorders involving dysregulation of a neurotransmitter as for example, in manic depression and schizophrenia. Imbalances of the autonomic nervous system can also be treated by the concurrent agonist-antagonist administration, as well. In particular, sympathetic nervous system disorders e.g. hypertension could also be treated by this approach with the adrenergic agonist-antagonist combinations.

The present invention also provides a unique composition of both an agonist and an antagonist. The composition is novel and unobvious in view of the fact that one would not normally attempt to combine an agonist and an antagonist for the reasons described above. Moreover, it is important to have a single composition which may be in tablet or pill form, for example, or which may be administered through a transdermal patch. In this way, the user who is typically an abuser of a drug or another agonist of that drug will not be able to separate the desired portion of the composition, namely the drug or agonist from the antagonist. When the user takes the composition, the user will receive both the drug or its other agonist and the antagonist to the drug.

This invention possesses many other advantages and has other purposes which will be made more clearly apparent from a consideration of the forms in which it may be embodied. They will now be described in more detail for purposes of illustrating the general principles of the invention, but it is to be understood that such detailed description is not to be taken in a limiting sense.

BRIEF DESCRIPTION OF THE DRAWINGS

Having thus described the invention in general terms, reference will now be made to the accompanying drawings (two sheets) in which:

DETAILED DESCRIPTION OF PREFERRED EMBODIMENTS

Referring now in more detail and by reference characters to the drawings, which illustrate several practical embodiments of the present invention, the invention relies in its principle aspect, upon the administration of a drug, or another agonist of the drug, and an antagonist to the drug, as previously described. As also indicated above, there are two major approaches to reduction of drug dependency using a combination of the agonist and an antagonist.

In the first of these approaches, an effective treatment strategy is based upon the combined administration of the agonist and an antagonist. The net result of the administration of the drug, or another agonist of that drug and its own antagonist is that even more receptors of the users brain for that drug are occupied than if either the agonist or the antagonist were given alone. As a result, the drug user is further insulated from any reinforcing effects of the abused substances. As an example, by administering a dose of nicotine and dose of mecamylamine, the user is insulated from the formerly desirable effects associated with the smoking of tobacco and which desired effects were primarily the obtaining of nicotine. Few receptors are left available to respond to the abused substance in this case because the receptor system is at least partially saturated.

It should be understood that the receptor system could only be partially saturated in that there could be serious adverse consequences to the patient or other subject if all of the receptors were occupied by either a drug or an agonist. Nevertheless, in the context of the present invention, a much larger number of receptors are occupied than would otherwise be occupied if the subject was receiving only a drug or other agonist and the antagonist.

A further advantage of this approach over the administration of an agonist alone, or an antagonist alone, is that the toxic effects of either drug are offset by the other. As a simple example, in the case of nicotine, it may not be safe to administer a sufficiently high dose of the nicotine to occupy enough receptors for obtaining a maximal suppression of an individual's craving for cigarettes. However, by concurrently administering an antagonist for the nicotine, such as mecamylamine, a higher dose of the nicotine could be administered. In like manner, it is possible to deliver a higher dose of a highly addictive drug, such as heroin or morphine, when naltrexone is administered.

The agonist and the antagonist are preferably simultaneously administered to the subject. However, it should be understood that the antagonist could be administered shortly after the administration of the agonist or otherwise, the agonist could be administered shortly after the administration of the antagonist. It is important, however, in the context of this mode of treatment that there is a generally similar therapeutic amount of the antagonist along with the agonist. In this way, the user will not suffer a severe withdrawal symptom which would otherwise occur with the presence of a large amount of the antagonist and a very small amount of the agonist. In like manner, the user will not be able to obtain the pharmacologic effects to which he or she was normally accustomed if there is not an excess of the agonist without a corresponding presence of a substantial amount of the antagonist.

Any means for delivering the agonist and the antagonist may be employed. For example, the agonist and the antagonist may be administered by means of a transdermal patch, as hereinafter described or it may be administered by means of a pill or tablet, or the like. Moreover, the agonist and an antagonist could be administered intravenously or by other means known for administration of medicaments e.g. sublingually, etc.

Figure 1:
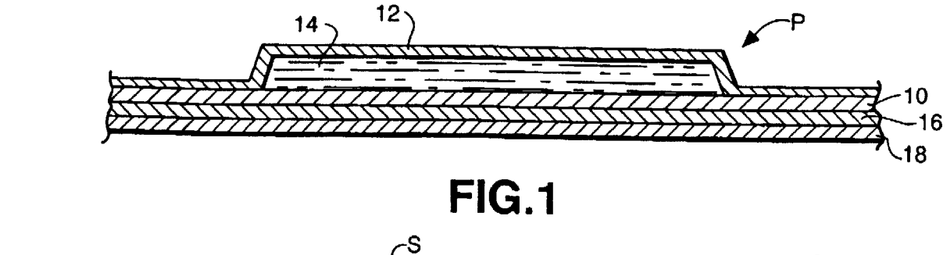
FIG. 1 is a somewhat schematic vertical sectional view of a transdermal patch for the transdermal administration of an agonist or an antagonist.

The preferred modes of administering the agonist or the antagonist and preferably both relies upon the use of a transdermal patch P of the type illustrated in FIG. 1 of the drawings. This patch P is adapted for application to a suitable portion of a smoker's body, as for example, on a forearm or a chest of the individual or the like.

The patch P comprises a lower liquid permeable membrane or layer 10 along with a suitable non-permeable covering or outer enclosing layer 12 and which forms a reservoir 14 therebetween. This reservoir 14 is sized to receive an agonist or an antagonist or both and which usually may be provided in a liquid form. The layer 10 may be provided on its under surface with an adhesive layer 16 covered by a releasable backing 18. Thus, when the releasable backing 18 is removed, the patch P can be adhered to the skin of a user through the adhesive layer 16. The adhesive layer 16 is also sufficiently porous so that any agonist or antagonist contained within the reservoir 14 may be transdermally applied to the user. In like manner, and for this purpose, small apertures could be formed within the adhesive layer 16, if desired.

The membrane 10 and the outer enclosing layer 12 may be formed of a cotton material or similar cloth-like material which is capable of retaining, but yet permitting dispensing of the agonist and antagonist or a liquid carrier which would hold the agonist and the antagonist. For this purpose, both the agonist and the antagonist may be liquid, or otherwise dissolved in a liquid carrier. The patch P may also be provided in the reservoir 14 with a silicone polymer matrix comprised of a cross-linked rubber and having micro-sealed compartments which are effectively formed by the cross-linking of the silicone rubber.

The exact details of construction of the patch P are not critical with respect to the present invention and other forms of dermally applicable patches can be used. One such patch is illustrated, for example, in U.S. Pat. No. 3,797,494 to Zaffaroni. Other patches which can be used are illustrated in U.S. Pat. No. 3,731,683 to Zaffaroni and U.S. Pat. No. 4,336,243 to Sanvordeker et al.

The patch P preferably has a size of about two centimeters by two centimeters at a minimum. Preferably, the patch has a surface area of about five centimeters by five centimeters with a thickness of about two to three millimeters. There is no effective outer limit on the size of the patch, except for convenience. When administering nicotine as the drug, the nicotine may be present in an amount so as to provide that amount of nicotine which would be acquired by a smoker. As a simple example, a patch could deliver a few milligrams of nicotine per hour. For a 24-hour delivery period the patch would have a size and thickness to retain about a minimum of 50 milligrams of nicotine.

In one of the preferred embodiments, when utilizing a transdermal patch, nicotine should be available so as to provide one to four milligrams per hour. The smoker normally obtains about two to about four milligrams per hour of nicotine as a result of a normal smoking pattern. Thus, at least the amount of nicotine to which the smoker is accustomed is generally present. The mecamylamine is present in an amount of 0.5 milligrams to about one milligram per hour delivery. These relative amounts of the nicotine and the mecamylamine are present at the start of any nicotine reduction program and may be reduced after a period of time. After a period of time, the nicotine is reduced to no more than one milligram of nicotine to be delivered per hour along with about 0.5 milligrams of mecamylamine.

The patch has been found to be highly effective in that it provides a steady rate of delivery of both the agonist and the antagonist. In this way, there are no excessive levels of either, as previously described. Oral time release capsules can also provide the same effect. However, better control is provided when using the transdermal patch. An oral spray such as an aerosol spray can be used to administer the nicotine and the mecamylamine or for that matter, the other agonists and antagonists. However, the delivery of nicotine through an oral spray could present a problem due to the harshness and the severe irritation which results in the respiratory tract when inhaled, although this may be mitigated by mecamylamine.

The patch described herein can be placed on any convenient area of the users skin, such as, the underside of the forearm of the user's body or on the chest of an individual. In this way, when the patch is applied to the user's body it will release a continuous supply of nicotine to the smoker.

The nicotine and/or the mecamylamine may be dissolved in an inert vehicle, such as, for example, K-Y jelly or any other liquid carrier which does not react with the body or with the nicotine or the other agonists and the mecamylamine and other antagonists. The vehicle must also readily permit transdermal migration of the nicotine and mecamylamine. One of the primary liquid carriers which may be used is water. However, various low molecular weight alcohols, such as ethanol, etc. could be used. In addition, glycerol, propylene glycol, petrolatum, etc. are effective carriers for the nicotine and mecamylamine.

The nicotine and mecamylamine are each added to the liquid carrier in an amount of about 3 percent by weight to about 10 percent by weight, particularly when water is the liquid carrier in this case the amount of the two components added to the carrier are limited by the solubility of the mecamylamine. The amount of nicotine and mecamylamine to be added to the carrier is a function primarily of the desired rate of delivery, as hereinafter described, and is, in turn, a function of e.g. patch size, pH of the carrier, etc.

The carrier preferably should have a pH of no higher than about eight or nine, although it can be made less basic or more acidic, as hereinafter described, in order to control nicotine penetration rates. Nicotine is well known to penetrate the intact skin, particularly at a pH of about seven or greater.

The amount of any agonist and any antagonist introduced into a liquid carrier is a function of the solubility of the components in the carrier as well as the desired rate of delivery. Moreover, patch construction to some extent will affect the rate of delivery.

The relative amounts of agonist and antagonist which are administered to a subject are functions their receptor occupancy. Thus, it is desirable to provide the relative amounts of agonist and antagonist which present an equivalent amount of binding at the brain receptors for the agonist.

It is also possible to add to the liquid carrier an agent to increase the permeability of the skin, such as dimethyl sulfoxide (DMSO) or equivalent agent. The dimethyl sulfoxide is a topical agent which facilitates penetration of the agonist through the skin. Other similar acting agents which can be used include, e.g. sodium lauryl sulfate, 1-dodecylhexahydro-2H-azepin-2-one (Azone) and a mixture of propylene glycol and oleic acid.

The patch P has been found to be effective in administering either the antagonist or the agonist and preferably both in this embodiment of the invention. The patch is preferable inasmuch as it may provide a controlled rate of delivery of the agonist and antagonist to the user and also maintain a sustained level of the agonist and antagonist in the users bloodstream. By controlling the membrane size and like factors, it is possible to regulate the rate of delivery of these ingredients to the user. Moreover, the patch provides the desired pharmacologic effects to which the user is accustomed, but still blocks the need for the additional external administration of the drug. It also enables a disassociation of the convenient means for delivery of the drug. A person addicted to nicotine is accustomed to smoking as a means to derive that nicotine. When the patch is employed, there is no longer a reinforcement of the need for smoking to obtain the desired level of nicotine. In the case of a heroin addict who utilizes an intravenous needle, there is a disassociation in that the intravenous mode of administration is no longer required.

The second approach for treatment of drug dependencies utilizing the agonist and antagonist combinations relies upon an inverse conditioning for smoking cessation. This approach differs from the previously described approach in that the aim of the first approach is to saturate the nicotine receptors to thereby insulate the user from the reinforced effects of taking a drug. In this latter approach, the invention counter-conditions the stimuli associated with the administration of that drug by reversing the usual consequences of taking the drug.

In one of the preferred embodiments of the invention utilizing this latter approach of counter-conditioning, the drug or the agonist is applied to the individual in a level which would approximate that previously obtained by the individual. For example, the addict of heroin or morphine would receive methadone as the agonist to heroin or the morphine since methadone has a more constant systemic level. The methadone would be administered in amounts which would approximate the pharmacologic effects to which the individual was previously accustomed if the antagonist were not administered. In like manner, the party addicted to nicotine would receive that general level of nicotine to which he or she was previously accustomed. The administration of the nicotine or the other drug would preferably occur by any convenient means which was different than the addicted patients usual form of administration. Thus, the morphine or heroin could be taken through the oral cavity if the subject previously used intravenous delivery. The nicotine would preferably be applied by means of a transdermal patch. When a desired amount of the agonist has been assimilated into the system of the user, the user is then provided with a means for administration of the antagonist which would simulate the method previously used for taking the abused drug. In this case, for example, the user would be provided with naltrexone or otherwise naloxone in hypodermic needles, if in the past, the user had been accustomed to self-administering the morphine or heroin intravenously. Thus, the naltrexone would also be administered intravenously. It can be appreciated that when the user formerly administered a substance, he or she received a certain desired sensation. In this case, when the naltrexone is administered, there is an inverse conditioning in that there would be an unpleasant effect of withdrawal. The more that the user attempted to reinforce his or her habit by using intravenous needles, there would be a greater withdrawal. As a result, there is an inverse conditioning.

The same holds true in the case of the party addicted to nicotine. The act of smoking would then be negatively correlated with nicotine effects. The typical smoker is accustomed to receiving a nicotine reinforcement or so-called "high" by drawing puffs of smoke from a cigarette, a pipe, or other means for burning tobacco. In this case, the smoker is administered nicotine chronically through a transdermal patch or equivalent method of delivery other than by smoking. The smoker would also be provided with an artificial cigarette or other smoking device which contains mecamylamine as opposed to nicotine. In this case, the usual conditioning associated with smoking, namely increased nicotine stimulation and the pleasurable effects derived therefrom would not be obtained. In fact, there would be a withdrawal and in this paradigm, smoking would be associated with decreased nicotinic stimulation and the unpleasant effects of withdrawal. Thus, whenever the user smoked the artifical cigarette or similar smoking device, the user would be provided with the full range of sensory and motor aspects of smoking associated not with an increase, but rather a decrease in nicotine-induced satisfaction. The satisfaction provided by the systemic level of nicotine would be lessened by each bolus of mecamylamine that is inhaled.

Figure 6:
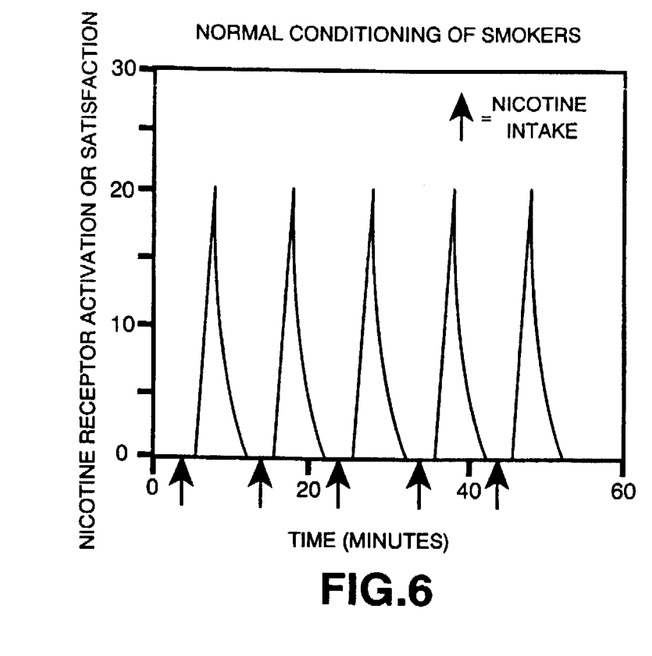
FIG. 6 is a graph showing a normal conditioning of a smoker with nicotine receptor activation as a function of time.
Figure 7:
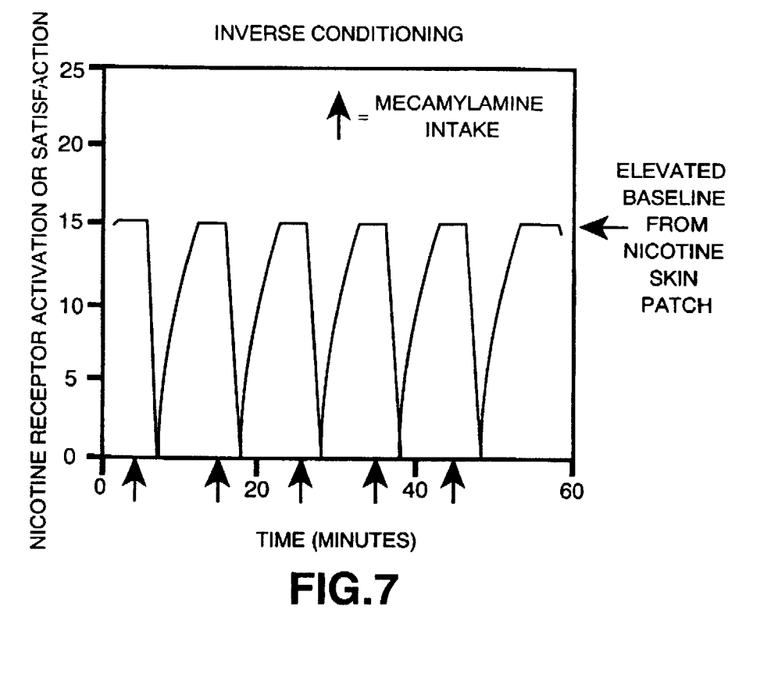
FIG. 7 is a graph showing an inverse conditioning of smokers with nicotine receptor activation as a function of time.

FIGS. 6 and 7 clearly show this effect of inverse conditioning. By reference to FIG. 6, the normal nicotine receptor activation or satisfaction is shown on a scale as a function of time. Each puff of a cigarette or similar smoking device provides a certain level of satisfaction since each puff of the tobacco smoke provides the satisfying drug, nicotine. In the inverse conditioning as shown in FIG. 7, it can be observed that there is an elevated base line of nicotine in the subject's bloodstream. Thus, the subject is "pre-loaded" with nicotine from the transdermal patch. However, on each occasion when a puff of the artificial cigarette is taken, there is a decrease in the amount of the satisfaction obtained. Thus, in comparison, whereas an increase in satisfaction occurred with each puff, in FIG. 6, a decrease in the satisfaction results with each puff, as shown in FIG. 7.

Figure 2:
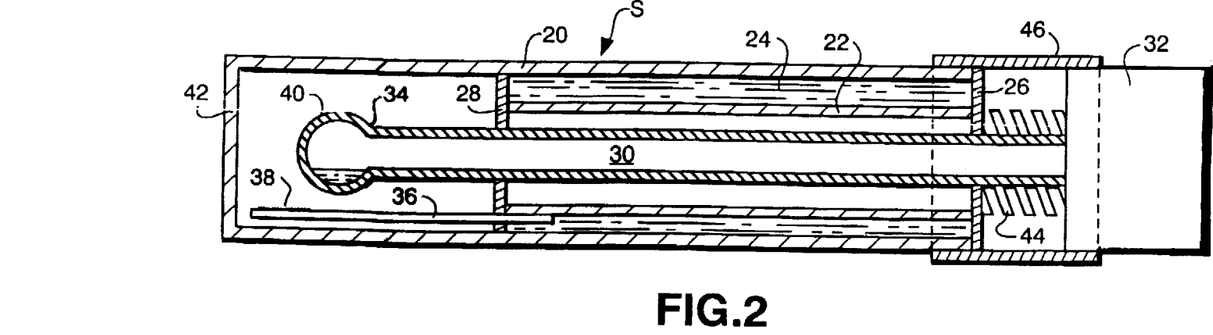
FIG. 2 is a vertical sectional view of an apparatus capable of being used for inhaling an aerosol of an agonist or an antagonist.

Those artificial smoking devices which are illustrated and described in the aforementioned patent application (Now. U.S. Pat. No. 4,846,199) could be used for the purposes of administering the antagonist in accordance with this embodiment of the invention. One such smoking device is illustrated in FIG. 2 of the drawings and comprises an outer housing 20 which may adopt the size and shape of a conventional cigarette. Thus the housing 20 is elongate and cylindrically shaped. Located within the housing 20 is a concentrically disposed, diametrically reduced cylindrically shaped divider 22 which forms an ignitable fluid chamber 24 containing a suitable ignitable fluid, such as a conventional lighter fluid e.g. liquid propane, butane, or the like. Any conventional petroleum distillate, such as conventional lighter fluids, may be employed for this purposed.

A pair of intermediate discs or walls 26 and 28 are located within the housing 20. Concentrically disposed within the divider tube 22 is an elongate smoke delivery tube 30. Mounted on the right hand end of the smoke delivery tube 30, reference being made to FIG. 2 is a filter 32 to create a draw or inhalation resistance, such as in a conventional cigarette filter. Located at the opposite end of the smoke delivery tube 30 is an enlarged ampule or reservoir 34 containing the antagonist, mecamylamine. The ampule 34 may be formed of glass or graphite or other inert material.

Extending from the chamber 24 containing the ignitable fluid is a wick 36 having an end 38 capable of being ignited to create a flame. However, by reference to FIG. 2, it can be observed that the ampule 34 is located in a position where it is not immediately above the flame of the burnable end 38 and therefore is not heated. When the smoker desires to create an aerosol of the constituents in the ampule 34, the smoke delivery tube 30 and hence the ampule 34 are shifted to the left, reference being made to FIG. 2. The constituents in the ampule 34 will become heated and form an aerosol.

The ampule 34 may be provided with an air inlet opening 40 so that when a suction is imparted to the ampule 34, through the smoke delivery tube 30, the aerosol will travel through the smoke delivery tube 30 and through the filter 32. A similar opening 42 may be formed in the end wall of the housing 20 for this purpose. The air inlet opening 42 also operates as a vent to prevent excessive pressure build-up within the ampule 34.

Thus, when the smoker desires to inhale, an aerosolized amount of a charge of the mecamylamine will be generated and inhaled, providing the negative effects described above. The user merely pushes on the smoke delivery tube 30 so that the ampule 34 is located over the flame of the burnable end 38 and within a matter of a few seconds, a sufficient amount of aerosol has formed, equivalent to that which would be generated in a puff by the smoker on a normal cigarette. This aerosol could even be visually similar to normal cigarette smoke. It could also be incorporated with agents to provide a similar aroma and other sensory qualities resembling cigarette smoke.

A spring 44 is disposed between the right-hand end wall 26 in the outer housing 20 and the filter 32. Moreover, an outer cover sleeve 46 is disposed over the spring between the filter 32 and the housing 20. The housing 20, as well as the sleeve 46, may both be formed of a suitable paperboard material which is relatively inexpensive so that the entire apparatus functions as a disposable cigarette which may be disposed of when the charge of antagonist in the ampule 34 has been depleted. Otherwise, the entire apparatus of FIG. 2 could be constructed to be reusable with the ampule capable of being recharged.

It is possible to generate the aerosol at a relatively low temperature by boiling the liquid antagonist solution, namely mecamylamine solution. For example, temperatures as low as 200 degrees C. could be used for generating a vapor and hence an aerosol of the condensate. Consequently, there is no significant combustion and hence poisonous products of combustion. Alternatively, a nebulizer such as an ultrasonic nebulizer could be used to create the aerosol to thereby eliminate any heating of the contents of the ampule.

Figure 3:
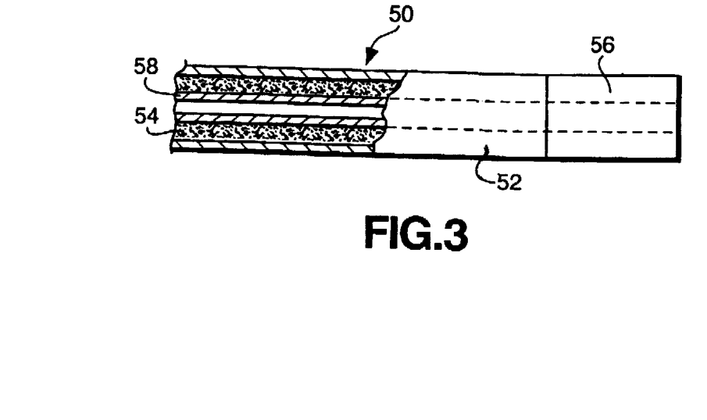
FIG. 3 is a schematic side elevational view, partially broken away and in section, and showing a modified form of apparatus for inhaling an aerosol of an agonist or an antagonist.

FIG. 3 illustrates a modified form of an apparatus for smoking of an antagonist, such as mecamylamine, and which comprises a conventional filter tipped cigarette 50 comprised of a paper tube 52 filled with ground tobacco 54. A conventional filter 56 is provided at the right-hand end of the cigarette in a conventional manner. The present invention provides an elongate tube 58 extending concentrically within the cigarette from one end thereof to the other and which is opened at each of the opposite ends. The tube 58 may also be formed of a paper material or similar burnable substance.

The tube 58 is provided on its interior with an antagonist such as mecamylamine. In this case, the antagonist could be in the form of a heavy gel which is coated on the interior surface of the tube 58. The burning cigarette 50 will provide the source of heat which will volatilize the mecamylamine. thus, as the left-hand end of the cigarette is ignited, the heat from the burning end of the cigarette will volatilize the mecamylamine enabling the mecamylamine to be inhaled by the smoker upon puffing at the filter 56.

In accordance with the construction illustrated in FIG. 3, it can be observed that there is very little draw resistance through the tube 58. Approximately 90 percent of any intake of the aerosol or smoke will be through the tube 58. While any drawing of air through the burning end of the cigarette will indeed produce cigarette smoke, this will be in a relatively small quantity. Nevertheless, this embodiment of the invention is effective in that it will provide some nicotine to the user so that there may not be a complete withdrawal syndrome. Thus, the device could be constructed so that the amount of nicotine which is generated can be proportioned to the amount of the antagonist, mecamylamine. In this way, it is possible to tailor the device to the particular needs of an individual in which smoking cessation is desired. This type of smoking apparatus is also effective in that it will have the feel and appearance of a conventional cigarette and will also enable the smoker to receive unaltered cigarette smoke along with the antagonist. If the amount of the antagonist is substantially greater than the amount of cigarette smoke, there still will be a net effect of a withdrawal. This further reinforces the decrease in nicotine-induced satisfaction.

Figure 4:
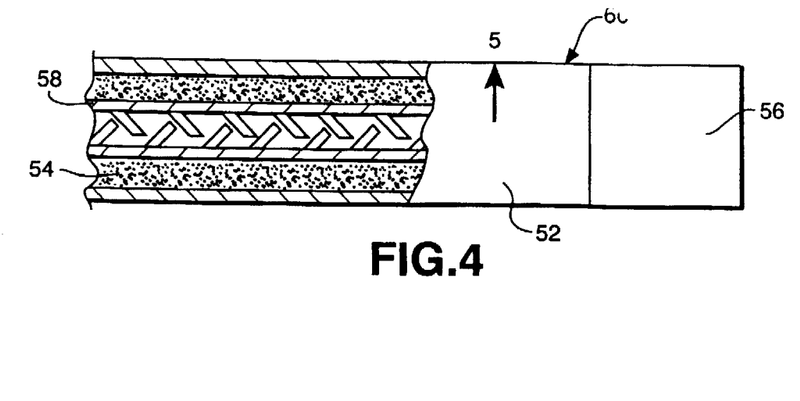
FIG. 4 is a schematic side elevational view, partially broken away and in section, and showing another modified form of apparatus for inhaling an aerosol of an agonist or an antagonist.
Figure 5:
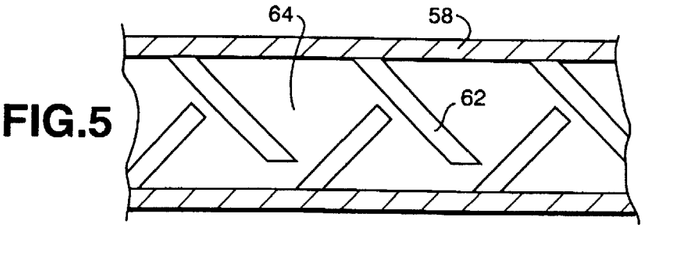
FIG. 5 is a fragmentary sectional view taken along line 5—5 of FIG. 4.

FIGS. 4 and 5 illustrate another modified form of smoking device 60 and which is very similar in construction to the smoking device 50 of FIG. 3 in that it employs a conventional filter tip cigarette. In this embodiment, the elongate smoke delivery tube 58 is provided on its interior surface with a plurality of radially inwardly extending somewhat flexible fingers 62. These fingers may actually adopt the form of filaments and are sufficiently flexible so as to yield to the draw of aerosol through the delivery tube 58. The fingers 62 generally extend randomly throughout the annular interior surface of the delivery tube 58 and are effective to preclude any of the liquid antagonist from rolling out of the delivery tube 58 when the cigarette is held in a vertical position with the outer end located downwardly. Thus, the liquid antagonist will collect in the spaces 64 between the point of connection of the fingers 62 and the interior surface of the wall of the tube 58.

It can be observed that the smoking device 60 is also effective in generating an aerosol or smoke of the antagonist similar to the device in FIG. 3. Thus, this device would also be effective in increasing the negative effect associated with the smoking of a cigarette.

It can be observed in connection with this approach for reducing the dependence on drugs, and in particular nicotine, that there is an inverse conditioning to tobacco smoke whereby the act of smoking is negatively correlated with nicotine effects. The smoker is given nicotine through the patch or other means as aforesaid and the mecamylamine is obtained through an artificial cigarette which may simulate the appearance, size and shape of a conventional cigarette. As indicated above, this smoking would be associated with decreased nicotine stimulation and the unpleasant effects of withdrawal. As long as the subject did not resume tobacco smoking as through conventional cigarettes, this inverse conditioning would lessen the temptation provided by smoke from external sources, as for example from third parties cigarettes.

In the case of cocaine, amphetamines and other stimulants, an agonist such as bromocriptine could be used. The bromocryptine would typically be administered in an amount of about 40 to 100 milligrams per day. Again, this agonist could be taken orally or otherwise by means of a transdermal patch. However, with a transdermal patch, the bromocriptine agonist would typically be administered in a rate of about 10 to 25 milligrams per day. The antagonist for cocaine, amphetamines and these other stimulants would be fluphenazine such as fluphenazine hydrochloride. This fluphenazine hydrochloride would be taken at a rate of about 20 to 60 milligrams per day orally. In like manner, fluphenazine decanoate could also be used as an antagonist at a rate of about 25 to 75 milligrams in each three week period. This latter antagonist would be injected intramuscularly.

With respect to heroin and other opiates, the agonist is methadone and would normally be administered orally in an amount of about 30 to about 120 milligrams per day. The antagonist for the opiates is naltrexone, as aforesaid. The naltrexone would be administered in a rate of about 40 to about 70 milligrams per day. Again, the naltrexone could be administered orally or intravenously, although it is preferably administered intravenously to negatively correlate to the effects of the abused drug. It should be understood that other drug dependencies with drugs such as barbituates, benzodiazopines and alcohol could also be treated with this combination of agonist and antagonist treatment. Dangerous withdrawal symptoms would still be carefully monitored and controlled.

The invention is also effective in therapeutically treating psychophysiological diseases and disorders involving neuronal dysregulation and which may also involve a drug use. As indicated previously, psychiatric disorders which involve the dysregulation of a neurotransmitter including manic depression and schizophrenia could be treated by the method of the present invention. In this case, for treatment of psychiatric dysorders of this type, bromocriptine would be used as an agonist, generally in the amounts used for treatment of cocaine. The fluphenazine, or the other derivitives thereof, would be used as the antagonist, also in the ranges as indicated above.

Diseases involving the imbalances of the autonomic nervous system can also be treated by this agonist-antagonist drug administration. Sympathetic nervous system disorders, such as hypertension, could also be treated with administration of adrenergic agonists and antagonists. Parasympathetic nervous system disorders could also be treated with concurrent treatment of muscarinic cholonergic agonists and antagonists.

The present invention also provides a unique composition of the agonist and the antagonist as indicated above. This agonist and antagonist combination is effective and unique in that it would not be expected to provide the beneficial results described herein. One would assume that the agonist and antagonist would counter the effects of each other thereby providing essentially no effect whatsoever. However, it has been determined in accordance with the present invention that this combination of agonist and antagonist is highly beneficial as previously described. It is important to provide a composition to the user so that the user may not discard the antagonist and only resort back to the old habit of using the agonist. This is particularly true with the highly addictive drugs such as the opiates and the like. Thus, the composition of the invention is an important contribution to the practice of the method and is highly effective therefore.

EXAMPLES

The invention is further illustrated by but not limited to the following examples.

Example 1

Approximately three milligrams per hour of nicotine is administered to a subject having a nicotine dependency. The nicotine is administered by means of a transdermal patch applied to the forearm of the subject. Mecamylamine is also administered simultaneously through the same patch at a rate of 15 to 30 milligrams per day. It is found that this type of administration substantially occupies the receptors in the brain of the subject thereby reducing the desire for nicotine intake.

Example 2

In example 2 a subject having nicotine dependency is treated by administration of the agonist-antagonist combination in accordance with the present invention. In this case, the nicotine is administered to a subject through a transdermal patch such that there is about 20 nanograms of nicotine in each milliliter of the person's bloodstream at any point in time.

The subject is provided with a simulated cigarette or so-called artificial cigarette, similar to that illustrated in FIG. 3 of the drawings. The ampule of that artificial cigarette is provided with mecamylamine. When the user draws upon the filter of the cigarette, he receives a charge of mecamylamine Which causes a withdrawal effect. This, in turn, inversely conditions the smoker and ultimately causes the smoker to associate negative feelings with smoking of cigarettes thereby reducing the tendency of the smoker to resort to a smoking habit.

Example 3

A subject having a heroin addiction is treated by cessation of all heroin administration. The subject is provided with about 70 milligrams per day of methadone and which is administered orally simultaneously, the subject is also provided with naltrexone administered at a rate of about 50 milligrams per day and which is administered orally.

The brain receptors for these opiates are substantially filled thereby reducing the desire of the subject for further intake of heroin or an agonist thereof.

Thus, there has been illustrated and described a unique and novel combination of an agonist and an antagonist for treatment of drug dependency and other psychophysiological diseases and disorders. The present invention thereby fulfills all of the objects and advantages which have been sought therefore. It should be understood that many changes, modifications, variations and other uses and applications will become apparent to those skilled in the art after considering this specification and the accompanying drawings. Therefore, any and all such changes, modifications, variations and other uses and applications which do not depart from the spirit and scope of the invention are deemed to be covered by the invention.

Having thus described our invention, what we desire to claim and secure by letters patent is:

1. A pharmacologic composition for the treatment and reduction of dependency on an abused stimulating drug selected from the class consisting of cocaine and amphetamines where the addictive effects of this drug causes activation of receptors which are actuated by the drug, said composition comprising:

a) a bromocriptine agonist which causes receptors for the drug to become activated, said bromocriptine agonist being present in the composition in an amount to provide a daily dose of this agonist of 40 to 100 milligrams per day and thereby partially satiate the needs for the drug by a subject using the composition;

b) an antagonist selected from the class consisting of fluphenazine, fluphenazine hydrochloride and fluphenazine decanoate sufficient to at least partially block the effects of the drug, the receptors which are responsive to the drug also being sensitive to the antagonist, said amounts of the drug and the antagonist sufficient so that there is a substantial systemic amount of the antagonist present when there is a substantial systemic amount of the drug present in the blood of a user of the composition, the drug or the agonist and the antagonist when administered in said daily dose amounts will preclude intoxication or overdosing and also reduce a satisfaction of a subject when the drug is administered and also reduce a state of withdrawal from the drug in the subject, such that the drug or agonist is complemented by the antagonist to occupy a greater number of receptors of the subject using the drug than would be occupied by the drug alone.

2. The composition of claim 1 further characterized in that the drug and the antagonist are administered contemporaneously.

3. A pharmacologic composition for the treatment and reduction of dependency on an abused stimulating drug selected from the class consisting of cocaine and amphetamines where the addictive effects of the drug causes activation of receptors for the drug, said composition comprising:

a) a bromocriptine agonist which causes receptors for the drug to become activated, said bromocriptine agonist being present in the composition in an amount to provide a daily dose of this agonist in the amount of 10–25 milligrams per day through a transdermal patch and thereby partially satiate the needs for the drug by a subject using the composition;

b) an antagonist selected from the class consisting of fluphenazine, fluphenazine hydrochloride and fluphenazine decanoate with the fluphenazine and fluphenazine hydrochloride being present in an amount to provide a daily dose of 20–60 milligrams per day and the fluphenazine decanoate being present in an amount to provide 20–75 milligrams per three week period and being sufficient to at least partially block the effects of the drug and the antagonist being sufficient so that there is a substantial systemic amount of the antagonist present when there is a substantial systemic amount of the drug present in the blood of a subject using the composition, the drug or the agonist and the antagonist when administered in said daily dose amounts will preclude intoxication or overdosing and also reduce a satisfaction of a subject when the stimulating drug is administered and also reduce a state of withdrawal from the drug in the subject, such that the drug or agonist is complemented by the antagonist to occupy a greater number of receptors of the subject of the drug than would be occupied by the drug alone.

4. The composition of claim 3 further characterized in that the drug and the antagonist are administered contemporaneously.

5. A pharmacologic composition for the treatment and reduction of dependency on an abused stimulating opiate drug where the addictive effects of this drug causes activation of receptors for the drug, said composition comprising:
   a) a methadone agonist which causes receptors for the drug to become activated, said methadone agonist being present in the composition in an amount to provide a daily dose of this agonist at 30–70 milligrams per day and thereby partially satiate the need for the drug by a subject using the composition;
   b) a naltrexone antagonist present in an amount to provide a daily dose of about 40–70 milligrams per day and sufficient to at least partially block the effects of the drug, the receptors which are responsive to the drug also being sensitive to the antagonist, said amounts of the drug and the antagonist being sufficient so that there is a substantial systemic amount of the antagonist present when there is a substantial systemic amount of the drug present in the blood of a subject using the composition, the number of receptors of the subject which are activated by the drug or agonist and blocked by the antagonist being greater than the number of receptors which would be occupied by the agonist alone or antagonist alone.

6. The composition of claim 5 further characterized in that the agonist and the antagonist are administered contemporaneously.

7. A pharmacologic composition for the treatment of physiological dysfunction of a subject in which brain receptors of the subject are subject to under-activity and over-activity and where the composition reduces this under-activity and over-activity, said composition comprising a bromocriptine agonist in the composition in an amount to provide a daily dosage rate of 40 to 100 milligrams per day which prevents under-activity of the brain receptors causing this physiological dysfunction and an antagonist to the agonist present in the composition and being selected from the class consisting of fluphenazine, fluphenazine hydrochloride and fluphenazine decanoate, said fluphenazine antagonist or fluphenazine hydrochloride antagonist being present in the composition to provide a daily dosage rate of 20 to 60 milligrams per day and the fluphenazine decanoate if used present in an amount to provide a daily dosage ratio of 20–75 milligrams per day, and where the amounts of the antagonist are sufficient to prevent over-activity of the receptors and at least partially block the pharmacologic effects of the agonist, said amounts of agonist and antagonist being such that there is always a substantial systemic amount of the antagonist present when there is a substantial systemic amount of the agonist present in the subject using the composition and the receptor amounts also being sufficient to preclude intoxication and to also prevent under-activity of the receptors such that the agonist is complemented by the antagonist to occupy a number of receptors of the subject which is greater than the number of receptors which would be occupied by the agonist alone.

8. The composition of claim 7 further characterized in that the agonist and the antagonist are administered contemporaneously.

9. A pharmacologic composition for the treatment of physiological dysfunction of a subject in which brain receptors of the subject are subject to under-activity or over-activity and where the composition reduces the over-activity and under-activity, said composition comprising a bromocriptine agonist in the composition in an amount to provide a dosage rate of 10–25 milligrams per day by a transdermal patch which prevents under-activity of the brain receptors causing this physiological dysfunction and an antagonist to the agonist present in the composition and being selected from the class consisting of a fluphenazine, fluphenazine hydrochloride and fluphenazine decanoate, said fluphenazine antagonist or fluphenazine hydrochloride antagonist being present in the composition to provide a daily dosage rate of 20 to 60 milligrams per day and the fluphenazine decanoate if used present in an amount to provide a daily dosage rate of 20–75 milligrams per day and where the amounts of the antagonist are sufficient to prevent over-activity of the receptors and at least partially block the pharmacologic effects of the agonist, said amounts of agonist and antagonist being such that there is always a substantial systemic level of the antagonist present in the subject using the composition and the respective amounts also being sufficient so that the drug or agonist precludes intoxication and the combination of the agonist and antagonist also prevents under-activity of the receptors such that the agonist is complemented by the antagonist to occupy a number of receptors of the subject which is greater than the number of receptors which would be occupied by the agonist alone.

10. The composition of claim 9 further characterized in that the agonist and the antagonist are administered contemporaneously.

11. A pharmacologic composition for the treatment and reduction of dependency on an abused stimulating drug selected from the class consisting of cocaine and amphetamines where the addictive effects of this drug causes activation of receptors which are actuated by the drug, said composition comprising:
   a) an agonist selected from the class consisting of amphetamines and cocaine and bromocriptine which causes receptors for the drug to become activated, said agonist being present in the composition in an amount to provide a daily dose of this agonist of 40 to 100 milligrams per day and thereby partially satiate the needs for the drug by a subject using the composition;
   b) an antagonist selected from the class consisting of fluphenazine, fluphenazine hydrochloride and fluphenazine decanoate sufficient to at least partially block the effects of the drug, the receptors which are responsive to the drug also being sensitive to the antagonist, said amounts of the drug and the antagonist sufficient so that there is a substantial systemic amount of the antagonist present when there is a substantial systemic amount of the drug present in the blood of a user of the composition, the drug or the agonist and the antagonist when administered in said daily dose amounts will preclude intoxication or overdosing and also reduce a satisfaction of a subject when the drug is administered and also reduce a state of withdrawal from the drug in the subject, such that the drug or agonist is complemented by the antagonist to occupy a greater number of receptors of the subject using the drug than would be occupied by the drug alone.

12. The composition of claim 11 further characterized in that the drug and the antagonist are administered contemporaneously.

13. A pharmacologic composition for the treatment and reduction of dependency on an abused stimulating drug selected from the class consisting of cocaine and amphetamine where the addictive effects of the drug causes activation of receptors for the drug, said composition comprising:

a) an agonist selected from the class consisting of amphetamines and cocaine and bromocriptine which causes receptors for the drug to become activated, said agonist being present in the composition in an amount to provide a daily dose of this agonist in the amount of 10–25 milligrams per day through a transdermal patch and thereby partially satiate the needs for the drug by a subject using the composition;

b) an antagonist selected from the class consisting of fluphenazine, fluphenazine hydrochloride and fluphenazine decanoate with the fluphenazine and fluphenazine hydrochloride being present in an amount to provide a daily dose of 20–60 milligrams per day and the fluphenazine decanoate being present in an amount to provide 20–75 milligrams per three Week period and being sufficient to at least partially block the effects of the drug and the antagonist being sufficient so that there is a substantial systemic amount of the antagonist present when there is a substantial systemic amount of the drug present in the blood of a subject using the composition, the drug or the agonist and the antagonist when administered in said daily dose amounts will preclude intoxication or said daily dose amounts will preclude intoxication or overdosing and also reduce a satisfaction of a subject when the stimulating drug is administered and also reduce a state of withdrawal from the drug in the subject, such that the drug or agonist is complemented by the antagonist to occupy a greater number of receptors of the subject of the drug than would be occupied by the drug alone.

14. The composition of claim 13 further characterized in that the drug and the antagonist are administered contemporaneously.

15. A pharmacologic composition for the treatment of physiological dysfunction of a subject in which brain receptors of the subject are subject to under-activity and over-activity and where the composition reduces this under-activity and over-activity, said composition comprising an agonist selected from the class consisting of amphetamines and cocaine and bromocriptine in the composition in an amount to provide a daily dosage rate of 40 to 100 milligrams per day which prevents under-activity of the brain receptors causing this physiological dysfunction and an antagonist to the agonist present in the composition and being selected from the class consisting of fluphenazine, fluphenazine hydrochloride and fluphenazine decanoate, said fluphenazine antagonist or fluphenazine hydrochloride antagonist being present in the composition to provide a daily dosage rate of 20 to 60 milligrams per day and the fluphenazine decanoate if used present in an amount to provide a daily dosage ratio of 20–75 milligrams per day, and where the amounts of the antagonist are sufficient to prevent over-activity of the receptors and at least partially block the pharmacologic effects of the agonist, said amounts of agonist and antagonist being such that there is always a substantial systemic amount of the antagonist present when there is a substantial systemic amount of the agonist present in the subject using the composition and the receptor amounts also being sufficient to preclude intoxication and to also prevent under-activity of the receptors such that the agonist is complemented by the antagonist to occupy a number of receptors of the subject which is greater than the number of receptors which would be occupied by the agonist alone.

16. The composition of claim 15 further characterized in that the agonist and the antagonist are administered contemporaneously.

17. A pharmacologic composition for the treatment of physiological dysfunction of a subject in which brain receptors of the subject are subject to under-activity or over-activity and where the composition reduces the over-activity and under-activity, said composition comprising an agonist selected from the class consisting of amphetamines and cocaine and bromocriptine in the composition in an amount to provide a dosage rate of 10–25 milligrams per day by a transdermal patch which prevents under-activity of the brain receptors causing this physiological dysfunction and an antagonist to the agonist present in the composition and being selected from the class consisting of a fluphenazine, fluphenazine hydrochloride and fluphenazine decanoate, said fluphenazine antagonist or fluphenazine hydrochloride antagonist being present in the composition to provide a daily dosage rate of 20 to 60 milligrams per day and the fluphenazine decanoate if used present in an amount to provide a daily dosage rate of 20–75 milligrams per day and where the amounts of the antagonist are sufficient to prevent over-activity of the receptors and at least partially block the pharmacologic effects of the agonist, said amounts of agonist and antagonist being such that there is always a substantial systemic level of the antagonist present in the subject using the composition and the respective amounts also being the composition and the respective amounts also being sufficient so that the drug or agonist precludes intoxication and the combination of the agonist and antagonist also prevents under-activity of the receptors such that the agonist is complemented by the antagonist to occupy a number of receptors of the subject which is greater than the number of receptors which would be occupied by the agonist alone.

18. The composition of claim 17 further characterized in that the agonist and the antagonist are administered contemporaneously.

* * * * *